United States Patent [19]

Khayat

[11] Patent Number: 4,905,682
[45] Date of Patent: Mar. 6, 1990

[54] PROCEDURE AND FACILITIES FOR THE PROLONGED BLOOD-LETTING ON ANIMALS

[75] Inventor: David Khayat, Paris, France

[73] Assignee: Plastik Fur Die Medizin GmbH, Fed. Rep. of Germany

[21] Appl. No.: 182,607

[22] Filed: Apr. 18, 1988

[30] Foreign Application Priority Data

Dec. 12, 1987 [DE] Fed. Rep. of Germany ....... 3742263

[51] Int. Cl.$^4$ .............................................. A61M 5/32
[52] U.S. Cl. .......................................... 604/175; 604/9
[58] Field of Search ...................... 604/93, 175, 891.1, 604/8–10,185, 246, 212, 174, 891

[56] References Cited

U.S. PATENT DOCUMENTS

| 3,402,710 | 9/1968 | Paleschuck | 604/175 |
| 4,710,167 | 12/1987 | Lazorthes | 604/175 |
| 4,772,270 | 9/1988 | Wiita et al. | 604/175 |
| 4,784,646 | 11/1988 | Feingold | 604/175 |

FOREIGN PATENT DOCUMENTS

| 0119596 | 9/1984 | Fed. Rep. of Germany | 604/175 |
| 0134745 | 3/1985 | France | 604/175 |

Primary Examiner—Stephen C. Pellegrino
Assistant Examiner—William Lewis
Attorney, Agent, or Firm—William A. Drucker

[57] ABSTRACT

In a method for permanent blood removal from animals, especially small animals, a catheter is inserted into the blood-stream of the animal and a small extraction device is implanted under and/or on the skin, from which small extraction device blood is removed by means of a syringe/needle and/or through which prolonged intravenous perfusion and/or a repeatable injection is effected.

The implantable extraction device with catheter is formed of a bowl-shaped housing with at least one outer fixing rim with holes, a catheter connected thereto and at least one pierceable membrane closing the small-volume bowl chamber.

5 Claims, 1 Drawing Sheet

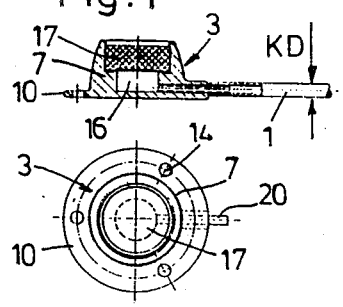
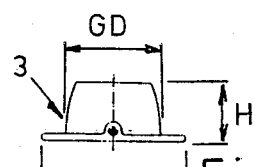
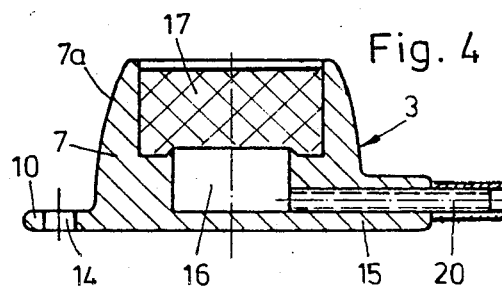
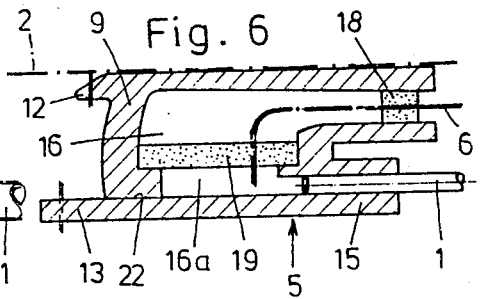
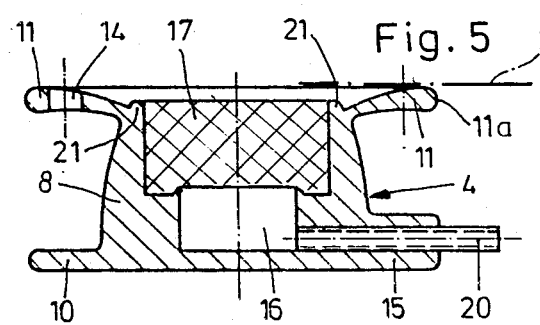
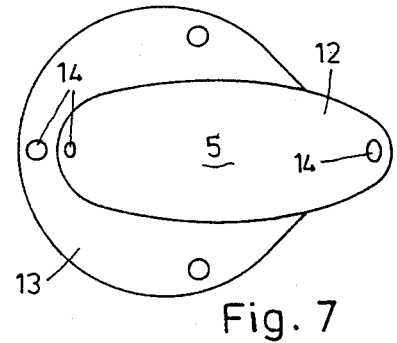
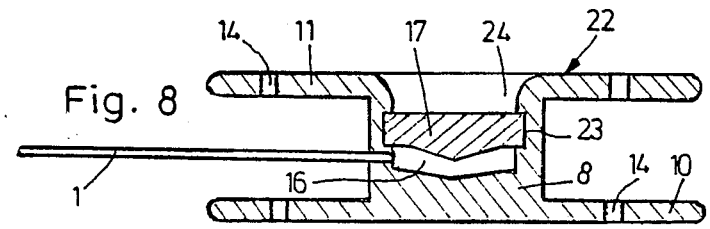

PROCEDURE AND FACILITIES FOR THE PROLONGED BLOOD-LETTING ON ANIMALS

SUMMARY OF THE INVENTION

The invention aims at the creation of a promising procedure for the prolonged blood-letting and/or prolonged intravenous perfusion and/or repeated injections on animals, especially small animals, and a straightforward, cost-saving produceable device which can be implanted in small animals in order to conduct this procedure.

The requirement for the procedure is being solved by the characteristics of patent claim No. 1 and, the requirements for the item by the characteristics of patent claim No. 2 whereby, for the animal-suited implantation—the characteristics of the sub-claims represent the advantageous furthering in solving these duties.

Subject matter of the invention does not only comprise the characteristics of each individual claim but also the combination thereof.

The invention created an implantable extraction device with catheter which, in its size and special design is meant for prolonged blood-letting and/or prolonged intravenous perfusion as well as frequent and/or repeated injection at small animals which can be so performed to its optimum.

The animal-suited implantation of the extraction device by means of specially designed fixing-rims enables its fixing underneath and/or on the skin of the small animals.

The extraction device shows furthermore advantageously arranged, pierceable membranes in which a specially formed needle can be fixed at one location which remains fixed even upon unexpected movements of the animal.

In addition, these membranes avoid blood-congestion or blood-coagulations within the chamber of the extraction device so that no disturbances may occur at prolonged blood-letting perfusion and/or injection.

BRIEF DESCRIPTION OF THE DRAWINGS

The drawings reflects working samples according to the invention described as follows:

FIGS. 1 to 3 is a vertical cut, a side view and the top view of a an extraction device outlined almost in original size;

FIG. 4 is a vertical cut through the extraction device according to FIGS. 1 to 3 enlarged:

FIG. 5 is a vertical cut through an extraction device of another design also enlarged;

FIG. 6 is a vertical cut through a an extraction device of a third design also enlarged;

FIG. 7 is a top view on the extraction device according to FIG. 6; and

FIG. 8 is a vertical cut through an extaction device having a small-chamber with a catheter directly connected thereto, on an enlarged scale.

DETAILS AND DESCRIPTION OF THE ILLUSTRATED EMBODIMENTS

A catheter is being introduced into the blood-stream (1) and a small extraction device (3 to 5) implanted under the animal skin (2) from which blood is taken with a syringe; this is the procedure of prolonged blood-lettig on small animals such as mice and rats, guinea-pigs, rabbits and bigger animals such as dogs, goats and monkeys. Prolonged perfusion as well as direct injection can also be done through the system.

A perfusion and/or injection can be effected through the extraction device (3 to 5) and the catheter (1), which broadens the use of the whole system.

The implantable extraction device (3 to 5) with catheter (1) have a bowl-shaped chamber (7,8,9) with at least one outside fixing-rim (10,11,12,13) with holes (14), one connector (15) for the catheter (1) and at least one pierceable membrane (18,19) covering the bowl-chamber (7,8,9), whereby the housing (7,8,9) has an outside diameter of approximately 15 mm, the fixing-rim (10 to 13) has and outside diameter of approximately 24 mm and the housing (7 to 9) with a fixing-rim (10 to 13) a total height of approximately 10mm as well as the catheter (1) and outside diameter of approximately 0.6 to 1.5 mm.

According to the first design as to FIGS. 1 to 4, the surrounding fixing-rim (10) is located at the lower end of the housing (7) and thus opposite the membrane (17), and shows an extension piece in form of a catheter-connection (15) in/on which a thin tube of metal, plastic or the like (20) is placed to connect the catheter (1) with the chamber (16).

This housing (7) shows, via the open side of the chamber (16) a basic-form narrowing from the fixingrim (10) causing the formation of a curved surface area (7).

The membrane (17) has an outside diameter of approximately 10 mm and a height of approximately 4 mm and lies with its piercing-side toward the upper side of the housing slightly backwards.

According to FIG. 5, the fixing-rim (11) is arranged at the side of the membrane (17) on the port-house (8) so that this extraction device (4) with its fixing-rim (11) may be fixed with sutures directly under or to the animal skin (2).

Since certain animals do not possess abdominal muscles to which the extraction device (4) could be fixed, the fixing-rim has been disposed at the upper portion of the device so it can be fixed to the animal skin (2).

The fixing-rim (11) surrounding the passage to the membrane (17) is provided, as can be seen, in the cross-section with a surrounding angular touch edge (21) whereby the user can easily locate this passage by touch when puncturing.

Furthermore, the fixing-rim (11) with its surrounding rim-edge (11a), is of a rounded contour toward the catheter connection (15), so that the animal skin (2) is not hurt during prolonged blood-letting perfusion.

This extraction device (4) possesses an additional fixing-rim (10) as shown in design FIG. 4.

The third design according to FIG. 6 and 7, the extraction device has two piercing-type-membranes (18,19) i.e. the one side membrane (18) and the one membrane (19) lying in the chamber (16) averting a blood accumulation and/or blood coagulation—for instance at aspiration, and diminishing the total volume of blood that will fill the chamber (16a) because of the very small volume of circulating blood contained in these small animals (i.e. mice).

From the side-membrane (18), a bent needle (6) is being introduced into the extraction device (5) which also penetrates the second membrane (19) at the same time, thus running into the lower chamber region (16a) which is indirect connection with catheter (1).

This second membrane (19) courses the total sealing/reduction of the chamber (16) into the true blood collecting chamber.

The extraction device interior is thus divided into two chambers (16, 16a), whereby blood loss is reduced to the volume of the smaller chamber (16a); this is especially important for small animals which have a small total quantity of blood, such as mice, for example, which have a blood quantity of less than 3 ccm.

This housing (9) is made for the installation of the two membranes (18,19) at least in split parts. The extraction device parts are formed to one unit by glueing, welding and so on. One partition-line of the port-house is indicated in FIG. 6 as (22).

This port (5) has an upper end and a lower fixing-rim (12,13) with holes (14) whereby the lower fixing-rim (13) shows a circular, and the upper fixing-rim (12) an oval basic form.

The membrane (18) is here lying at one side underneath the fixing-rim (12) within the port-house (9).

Because of the two membranes (18,19) and the bent and introduced needle (6), this needle cannot be stripped off by uninspected movements of the animal; it is safe and solidly anchored in the port (5). At this port (5), a catheter tube (1) is directly coming from the chamber (16a) through the connector (15).

Membranes (17,18,19) are designed in such a way that they will stand for approximately 100 to 1,000 punctures.

FIG. 8 shows another embodiment of a small chamber mini extraction device (22), which is constructed in principle in the same way as the extraction device (4) according to FIG. 5. A surrounding fixing rim (10,11) with holes (14) is formed on the housing (8) on each of the two sides (upper and lower). The housing (8) is cylindrical in form and forms an H cross-section with the two fixing rims (10,11).

A membrane (17) is inserted into the cavity of the housing (8) open from the fixing rim (11) and is held in a fixed position in the housing (8) in an annular groove (23). This membrane (17) lies deeper in the housing (8) than the fixing rim (11), such that on the one hand the extraction device fixing rimn (11) forms with the cavity of the port house (8) a feeler recess (24) from the outside of the fixing rim (11) to the piercing side of the recessed membrane (17) and the blood-collecting chamber (16) located under the membrane (17) is very small in volume.

A catheter (1) leads directly from the small-volume blood-collecting chamber (16) out of the (8), said catheter (1) being in direct connection with the housing (8), i.e. secured as a unit in the port house (8), whereby the blood from the catheter (1) can flow directly into the chamber (16).

The surrounding edges of the fixing rims (10,11) are rounded for gentle securing of the port (22) in the animal and below or under the animal skin.

Instead of the catheter (1) a needle (cannula) can also be secured in the housing (8), which needle is connected with the chamber (16) and connected with the housing (8) against any manipulation (such as displacement or the like).

The invention is based on two essential points, namely the new small-size extraction device construction and the arrangement of the fixing rim (11) at the housing side accessible from the membrane (17 or 18).

In this way it is achieved on the one hand that in the small-volume blood-collecting chamber (16, 16a) blood can be constantly and repeatedly removed from animals and on the other hand that through the membrane (16,16a) prolonged perfusion or repeated injection of fluids, for example, medicines) into animals can be effected, especially animals in which the easily accessible venous system is very limited.

The special construction of the extraction device (5) with two membranes (18,19) leads to two important advantages:

1. the volume of the catheter (1) connected to the smaller chamber (16a) can be reduced because of the very small circulating quantity of blood in small animals, for example, the extraction device chamber has a content of 330 $\mu$l. which corresponds to 10-20% of the entire blood content of a mouse;

2. and the needle (6) passed through the second membrane (18) is seated in a securely fixed position in the animal for prolonged perfusions and blood-letting.

The above is also valid for the construction according to FIG. 8 owing to the small chamber (16) and the small-volume catheter (1) firmly connected thereto or the needle connected with the chamber (16) and secured in the extraction device (22).

Because of these advantages the cost of the port in similar experiments can be covered by its being made possible to use smaller, cheaper animals compared with the current situation with larger animals, for example, mice instead of dogs. The care and feeding of smaller animals is cheaper.

I claim:

1. An implantable extraction device with a catheter for permanent blood sampling of animals particularly small animals, whereby the catheter is introduced into the animal blood stream and a small chamber of the device is implanted underneath the animals skin, from which by means of a canula or needle blood is removed or through which a protracted intravenous infusion or a repeated injection may be made, containing:
    (a) a bowl shaped housing for the chamber,
    (b) one pierceable membrane sealing the chamber on one side of the said housing,
    (c) a catheter fixed to a connection of the said housing,
    (d) an upper and a lower fixing rim on the housing with holes for optional fixing of the device to the animals skin or to the animals muscles,
    (e) a second pierceable membrane positioned in the chamber dividing the chamber into a smaller chamber connected with the catheter, the two pierceable membranes being disposed at an angle one to the other, and
    (f) a bent cannula or needle is fixed in position through in such a manner that it cannot be retracted.

2. An extraction device as claimed in claim 1 formed from at least two parts, its parts being adhered together.

3. An extraction device as claimed in claim 1 wherein the second membrane is disposed such as to define a lower chamber, and a catheter passes directly out of the lower chamber through the catheter connection.

4. An extraction device as claimed in claim 1 wherein the housing and the catheter are made of a plastic material suitable for implantation and the pierceable membranes are of silicon.

5. An implantable extraction device with a catheter for permanent blood sampling of animals particularly small animals, whereby the catheter is introduced into the animal blood stream and a small chamber of the device is implanted underneath the animals skin, from which by means of a canula or needle blood is removed or through which a protracted intravenous infusion or a repeated injection may be made, containing:
(a) a bowl shaped housing for the chamber,
(b) one pierceable membrane sealing the chamber on one side of the said housing,
(c) a catheter fixed to a connection of the said housing,
(d) an upper and a lower fixing rim on the housing with holes for optional fixing of the device to the animals skin or to the animals muscles, the lower fixing ring being circular in shape and the upper fixing ring being oval in shape, and
(e) a second pierceable membrane positioned in the chamber dividing the chamber into a smaller chamber connected with the catheter, and the first membrane being arranged under the upper fixing ring and above the second membrane in the housing.

* * * * *